United States Patent
Mullani

(10) Patent No.: US 10,441,379 B2
(45) Date of Patent: Oct. 15, 2019

(54) MULTIPURPOSE MEDICAL ILLUMINATOR WITH MAGNIFICATION

(71) Applicant: 3Gen, Inc., San Juan Capistrano, CA (US)

(72) Inventor: Nizar Mullani, Sugar Land, TX (US)

(73) Assignee: 3GEN, INC., San Juan Capistrano, CA (US)

( * ) Notice: Subject to any disclaimer, the term of this patent is extended or adjusted under 35 U.S.C. 154(b) by 0 days.

(21) Appl. No.: 15/856,606

(22) Filed: Dec. 28, 2017

(65) Prior Publication Data

US 2019/0201156 A1 Jul. 4, 2019

(51) Int. Cl.
*G02B 5/30* (2006.01)
*G02B 7/02* (2006.01)
(Continued)

(52) U.S. Cl.
CPC ............ *A61B 90/361* (2016.02); *A61B 90/35* (2016.02); *A61B 90/13* (2016.02); *A61B 2090/309* (2016.02); *G02B 25/02* (2013.01)

(58) Field of Classification Search
CPC ................ G02B 21/00; G02B 21/0004; G02B 21/0008; G02B 21/0016; G02B 21/0028; G02B 21/0032; G02B 21/0092; G02B 21/02; G02B 21/025; G02B 21/06; G02B 21/08; G02B 21/082; G02B 21/084; G02B 21/086; G02B 21/088; G02B 21/125;
(Continued)

(56) References Cited

U.S. PATENT DOCUMENTS

| 2,120,365 A | 6/1938 | Kriebel |
| 2,866,375 A | 12/1958 | Wells et al. |

(Continued)

FOREIGN PATENT DOCUMENTS

| IT | 01300568 | 10/1999 |
| JP | 04214523 | 12/1990 |
| WO | 2007034525 | 3/2007 |

OTHER PUBLICATIONS (Instruction Manual—English Portion) "DermLite II Fluid", 3Gen, LLC., 2006 (1 page).
(Continued)

*Primary Examiner* — Thong Q Nguyen
(74) *Attorney, Agent, or Firm* — Stetina Brunda Garred and Brucker

(57) ABSTRACT

The disclosure demonstrates a multipurpose illuminator used in medical examinations. The multipurpose illuminator described herein employs a housing incorporating two magnification viewing lenses each having different powered magnification that allows medical practitioners to view patient tissue and structures using two different magnifications. A battery power source is also contained in the housing to provide power to an illumination source. The illumination source may include an array of LEDs to provide light for viewing the patient tissue and matter. The illumination source and the lenses may be cross polarized relative to each other to provide enhanced viewing of the patient tissues and structures. A switch is provided to initiate the LED illumination source or to provide modes of operation that provide certain of the LEDs being illuminated.

22 Claims, 8 Drawing Sheets

(51) Int. Cl.
*A61B 90/00* (2016.01)
*A61B 90/35* (2016.01)
*A61B 90/30* (2016.01)
*G02B 25/02* (2006.01)
*A61B 90/13* (2016.01)

(58) Field of Classification Search
CPC ........ G02B 21/14; G02B 21/18; G02B 21/20;
G02B 21/22; G02B 7/00; G02B 7/02;
G02B 7/021; G02B 5/30; G02B 25/02;
A61B 90/13; A61B 90/35; A61B 90/361
See application file for complete search history.

(56) References Cited

U.S. PATENT DOCUMENTS

| | | | |
|---|---|---|---|
| 2,947,212 A | 8/1960 | Woods et al. | |
| 3,062,087 A | 11/1962 | Zandman et al. | |
| 3,519,339 A * | 7/1970 | Hutchinson | A61F 9/022 351/159.63 |
| 3,711,182 A | 1/1973 | Jasgur | |
| 4,007,979 A | 2/1977 | Coblitz | |
| 4,398,541 A | 8/1983 | Pugliese | |
| 4,538,889 A | 9/1985 | Heine et al. | |
| 4,773,097 A | 9/1988 | Suzaki et al. | |
| 4,846,184 A | 7/1989 | Comment et al. | |
| 4,957,368 A | 9/1990 | Smith | |
| 4,998,818 A | 3/1991 | Kugler et al. | |
| 5,146,923 A | 9/1992 | Dhawan | |
| 5,198,875 A | 3/1993 | Bazin et al. | |
| 5,343,536 A | 8/1994 | Groh | |
| 5,363,854 A | 11/1994 | Martens et al. | |
| 5,492,118 A | 2/1996 | Gratton et al. | |
| 5,561,563 A * | 10/1996 | Chesnut | F41G 1/383 359/822 |
| 5,690,417 A | 11/1997 | Polidor et al. | |
| 5,742,392 A | 4/1998 | Anderson et al. | |
| 5,760,407 A | 6/1998 | Margosiak et al. | |
| 6,032,071 A | 2/2000 | Binder | |
| 6,069,565 A | 5/2000 | Stern et al. | |
| 6,081,612 A | 6/2000 | Gutkowicz-Krusin et al. | |
| 6,118,476 A | 9/2000 | Morito et al. | |
| 6,207,136 B1 | 3/2001 | Matsuoka | |
| 6,384,988 B1 | 5/2002 | Muller et al. | |
| 6,396,532 B1 * | 5/2002 | Hoover | G02B 21/362 348/79 |
| 6,483,247 B2 | 11/2002 | Edwards et al. | |
| 6,587,711 B1 | 7/2003 | Alfano et al. | |
| 6,842,635 B1 | 1/2005 | Parker | |
| 7,004,599 B2 | 2/2006 | Mullani | |
| 7,006,223 B2 | 2/2006 | Mullani | |
| 7,027,153 B2 | 4/2006 | Mullani | |
| 7,151,956 B2 | 12/2006 | Satoh et al. | |
| 7,167,243 B2 | 1/2007 | Mullani | |
| 7,167,244 B2 | 1/2007 | Mullani | |
| 7,220,254 B2 | 5/2007 | Altshuler et al. | |
| 7,400,918 B2 | 7/2008 | Parker et al. | |
| 7,621,653 B2 | 11/2009 | Hendrie | |
| 7,841,751 B2 | 11/2010 | Mulani | |
| 7,874,698 B2 | 1/2011 | Mullani | |
| 7,986,987 B2 | 7/2011 | Bazin et al. | |
| 8,496,695 B2 | 7/2013 | Kang et al. | |
| 8,498,460 B2 | 7/2013 | Patwardhan | |
| 8,588,605 B2 | 11/2013 | Harris | |
| 8,849,380 B2 | 9/2014 | Patwardhan | |
| 9,182,343 B2 | 11/2015 | Goldfain | |
| 9,314,149 B2 | 4/2016 | Vivenzio et al. | |
| 9,345,430 B2 | 5/2016 | Nakamura et al. | |
| 9,427,188 B2 | 8/2016 | Heine et al. | |
| 9,458,990 B2 | 10/2016 | Mullani | |
| 9,642,517 B2 | 5/2017 | Wood et al. | |
| 2003/0026110 A1 | 2/2003 | Satoh et al. | |
| 2003/0045799 A1 | 3/2003 | Bazin et al. | |
| 2004/0062056 A1 | 4/2004 | Heine et al. | |
| 2004/0201846 A1 | 10/2004 | Mullani | |
| 2008/0015663 A1 | 1/2008 | Mullani | |
| 2008/0065176 A1 | 3/2008 | Zhang et al. | |
| 2009/0093761 A1 | 4/2009 | Sliwa et al. | |
| 2011/0270200 A1 | 11/2011 | Edgar et al. | |
| 2011/0304705 A1 | 12/2011 | Kantor et al. | |
| 2014/0012137 A1 | 1/2014 | Rosen | |
| 2014/0243685 A1 | 8/2014 | Patwardhan et al. | |
| 2014/0267882 A1 * | 9/2014 | O'Neill | H04N 5/2254 348/360 |
| 2014/0364745 A1 | 12/2014 | Patwardhan | |
| 2015/0374277 A1 | 12/2015 | Patwardhan | |

OTHER PUBLICATIONS (Instruction Manual—English Portion) "DermLite II Hybrid m", 3Gen, LLC., 2009 (1 page).

Keshen R. Mathura et al., "Comparison of OPS imaging and conventional capillary microscopy to study the human microcirculation," The American Physiological Society, vol. 91, p. 74-78, 2001 (5 pages).

(Brochure) 3gen, LLC., "First in Pocket Epiluminescence Microscopy," 1 page, Mar. 15, 2001 (Estimated publication date).

(Brochure) 3gen, LLC., "3gen the Beauty of Revolutionary Innovation," 3 pages (trifold), Feb. 15, 2002 (Estimated publication date) (6 pages).

Pan, Yan et al., "Polarized and Nonpolarized Dermoscopy The Explanation for the Observed Differences", American Medical Society, (Reprinted) Arch Dermatol, vol. 144 (No. 6), Jun. 2008 (2 pages).

Dhawan, Atam P. et al., "Multispectral Optical Imaging of Skin-Lesions for Detection of Malignant Melanomas", 31st Annual International Conference of the IEEE EMBS, Minneapolis, MN, USA Sep. 2-6, 2009, p. 5352-5355, 2009, (4 pages).

Arrazola, Peter et al., "Dermlite II: An Innovative Portable Instrument for Dermoscopy Without the Need of Immersion Fluids", Skin Med, Le Jacq Mar.-Apr. 2005; 10: p. 78-83 (6 pages).

Garcia-Uribe, Alejandro et al., "In-vivo characterization of optical properties of pigmented skin lesions including melanoma using oblique incidence diffuse reflectance spectrometry", Journal of Biomedical Optics, vol. 16 (2), p. 020501-1-020501-3, Feb. 2011 (3 pages).

(Flyer), Visomed, "MicroDERM Luminis The hand-held demoscope with daylight optics", Visiomed AG 2009, (2 pages).

(Instruction Manual—English Portion) "DermLite DL1", 3Gen, LLC., 2011 (1 page).

(Instruction Manual—English Portion) "DermLite II PRO HR", 3Gen, LLC., 2008 (1 page).

(Instruction Manual—English Portion) "DermLite II Pro", 3Gen, LLC., 2007 (1 page).

(Instruction Manual—English Portion) "DermLite DL3", 3Gen, LLC., 2009 (1 page).

(Instruction Manual- English Portion) "DermLite II Multispectral", 3Gen, LLC., 2004 (1 page).

(Instruction Manual—English Portion) "Lumio DermLite", 3Gen, LLC., 2007 (1 page).

(Instruction Manual—English Portion) "DermLite Foto Quickstart Guide", 3Gen, LLC., 2009 (1 page).

Barun, Vladimir V., "Absorption spectra and light penetration depth of normal and pathologically altered human skin", ResearchGate, (Website) Journal of Applied Spectroscopy, vol. 74 (No. 3), Mar. 2007 (11 pages). https://www.researchgate.net/publication/225598882.

Unknown (Internet Literature), www.syrisscientific.com, "Technical", 1 page, Web printout Feb. 24, 2003.

(Instruction Manual—English Portion) "DermLite carbon", 3Gen, LLC., 2008 (1 page).

Instruction Manual—English Portion) "DermLite cam Dermoscopy Camera", 3Gen, LLC., 2013 (1 page).

(Instruction Manual—English Portion) "DermLite DL100", 3Gen, LLC., 2008 (1 page).

"The physical basis for skin appearance is reflectance of light," (Internet Literature), www.syrisscientitic.com, 1 page, Web printout Feb. 24, 2003.

(56) References Cited

OTHER PUBLICATIONS

Wang, Hening et al., "Systematic Design of a Cross-Polarized Dermoscope for Visual Inspection and Digital Imaging," IEEE Instrumentation & Measurement Magazine, pp. 26-31, Dec. 2011.

* cited by examiner

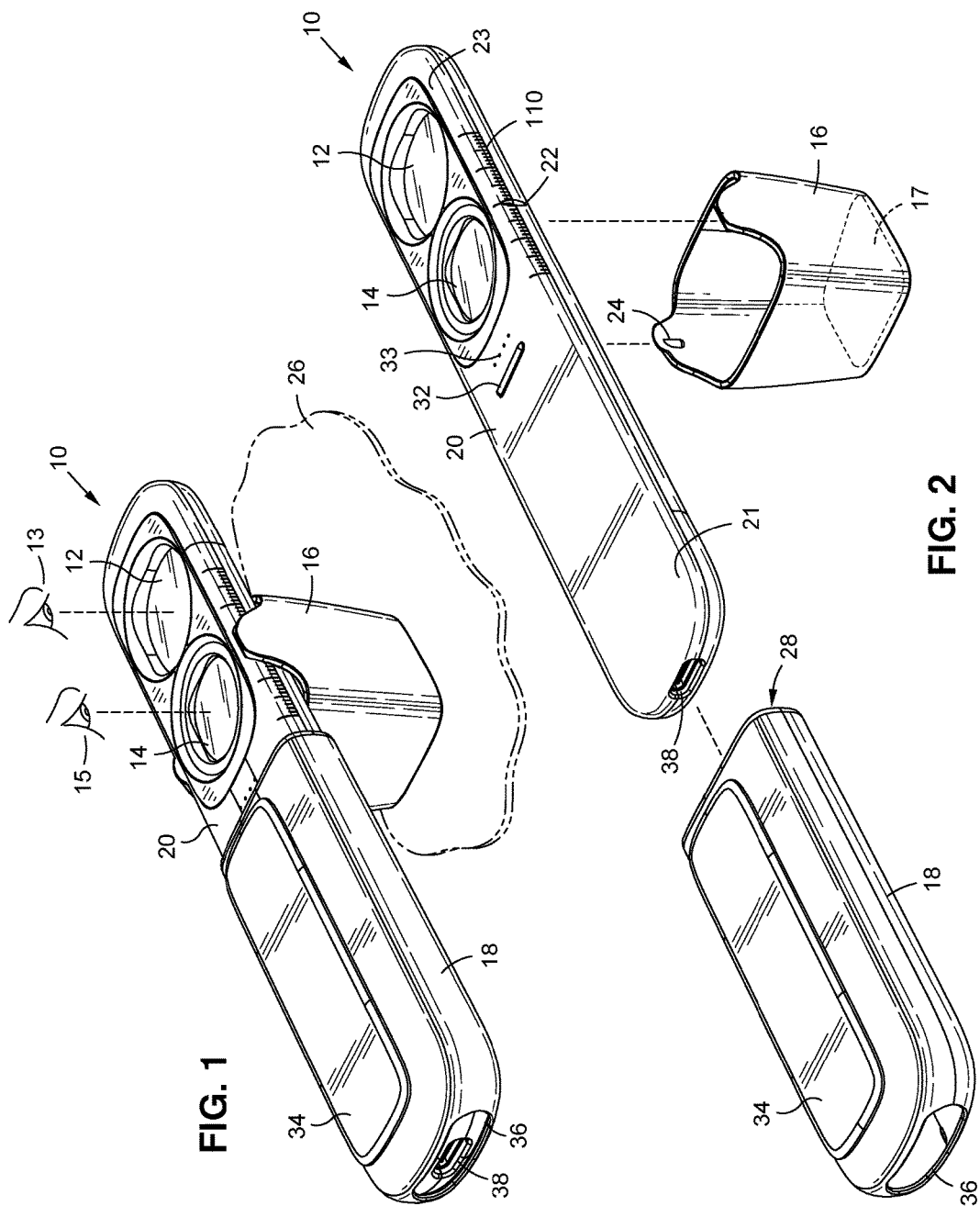

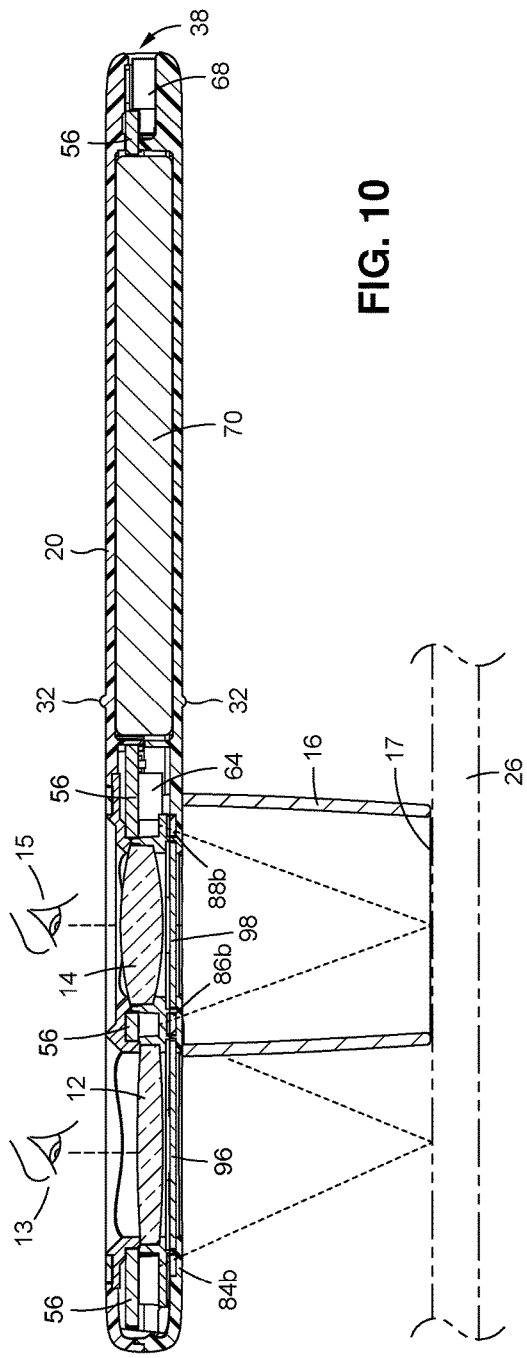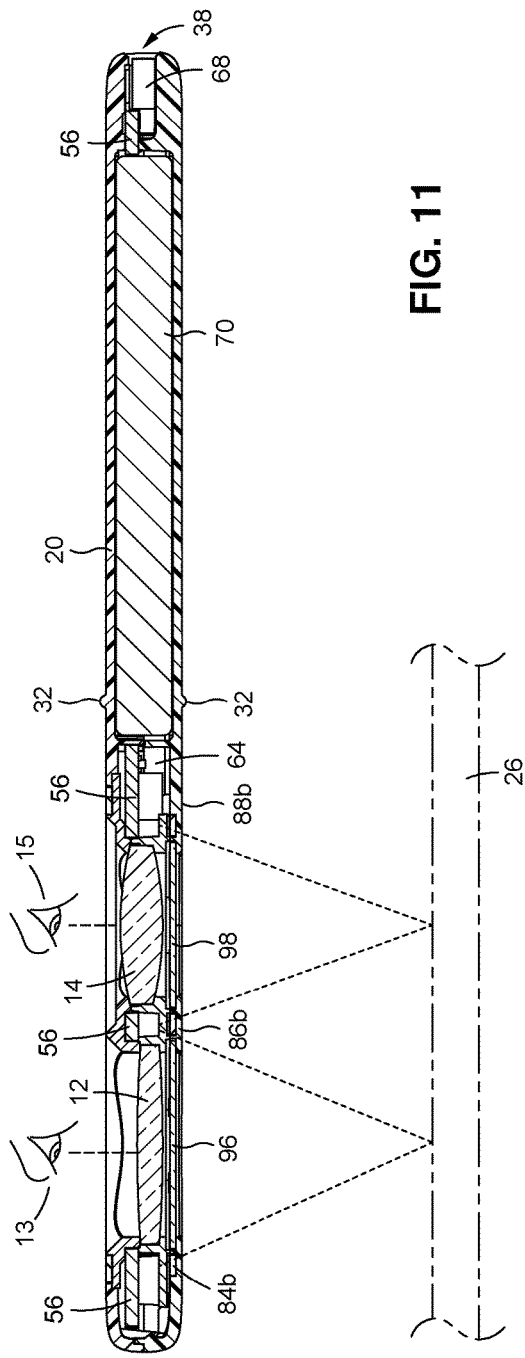

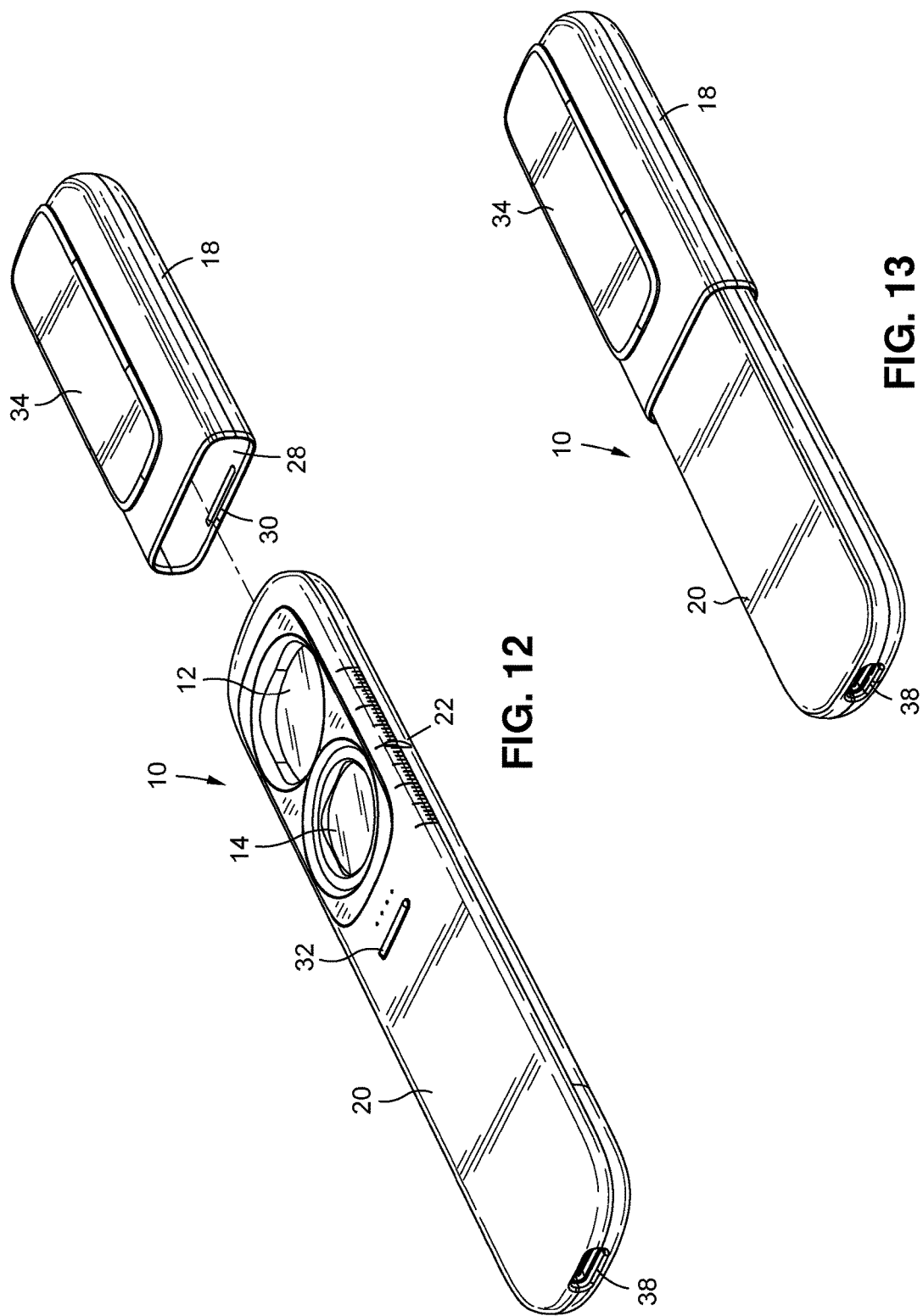

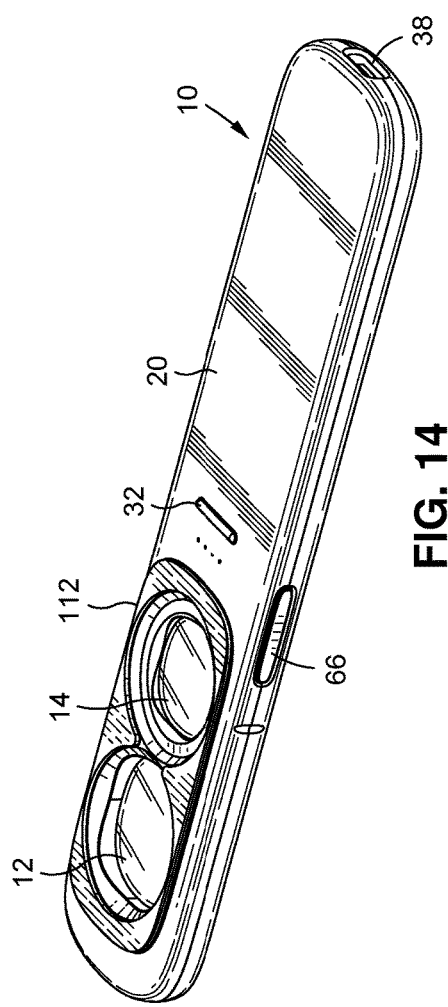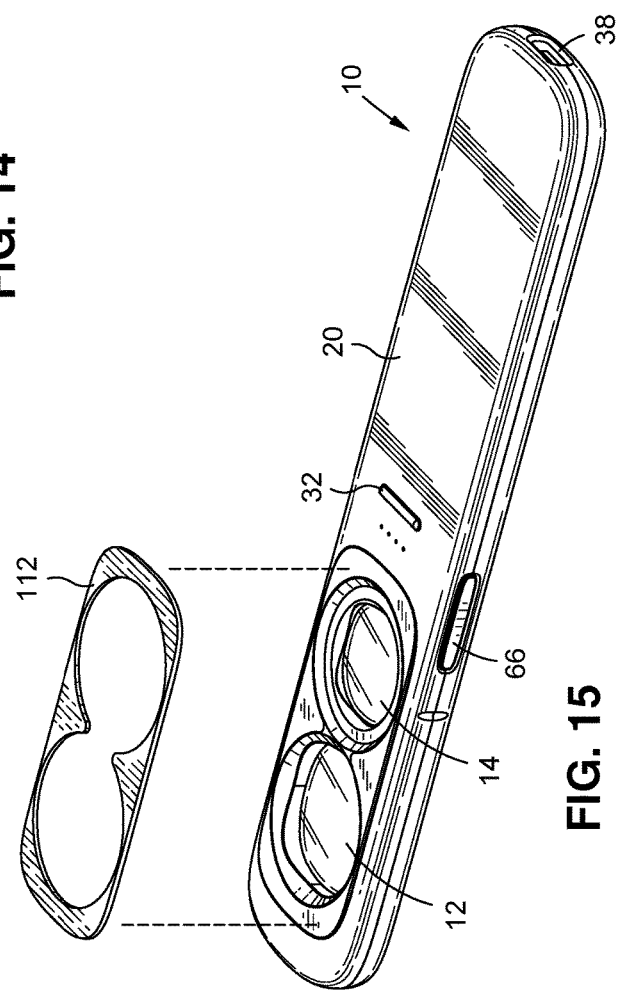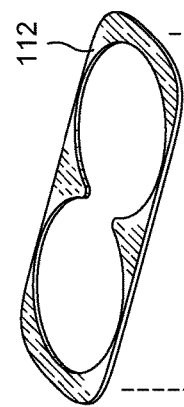

MULTIPURPOSE MEDICAL ILLUMINATOR WITH MAGNIFICATION

CROSS-REFERENCE TO RELATED APPLICATIONS

Not Applicable.

STATEMENT RE: FEDERALLY SPONSORED RESEARCH/DEVELOPMENT

Not Applicable

BACKGROUND

Technical Field

The present inventive subject matter relates generally to a hand-held illumination device used in medical examinations. More particularly, the inventive subject matter relates to an improved multipurpose apparatus for enhanced viewing and illumination for medical examinations using multiple magnifiers in conjunction with an arrangement of light emitting diodes.

Background

Medical examinations by physicians may employ the use of hand-held illuminators to assist the doctor in magnified and non-magnified viewing of the tissue of a patient. Hand-held illuminators without magnification include pen lights, which are widely used by general medical practitioners. Also, physicians and medical practitioners make use of hand-held illumination devices that have magnification including otoscopes, ophthalmoscopes and dermatoscopes. Otoscopes, ophthalmoscope and dermatoscopes include a single lens for magnification and are designed for particular types of examination. Also, standard otoscopes and ophthalmoscope do not employ polarization of light and viewing lenses.

Hand-held dermoscopy devices that use light with magnification can utilize polarizers or liquid-glass interfaces to reduce surface reflection and aid in viewing of deeper structures in the skin. Dermoscopy apparatuses that employ light polarization to aid in viewing human skin surfaces and deeper tissue and structures of the skin are known and described in U.S. Pat. No. 7,006,223 issued on Feb. 28, 2006 to Mullani, and U.S. Pat. No. 7,167,243 issued Jan. 23, 2007 to Mullani, the substance of each of which is wholly incorporated herein by reference. In addition, a dermoscopy device identified as Dermlite® DL3 device is manufactured and marketed by 3Gen, Inc. of San Juan Capistrano which uses light and polarization. In the Dermlite® DL3 hand-held device, a series of light emitting diodes ("LEDs") are concentrically positioned around a magnifying lens to assist in lighting of a magnified image. The device includes LEDs that provide reduced glare, cross-polarized light to aid in canceling the reflected light from the skin, and other LEDs on the device provide non-polarized light for traditional immersion fluid dermoscopy or for simply employing non-polarized light.

It is also well known that different colored light penetrates to different depths in human skin tissue. Specific color wavelengths are absorbed differently by different components of the skin tissue. Such use of colored LEDs in a dermatoscope is described in U.S. Pat. No. 7,027,153 issued on Apr. 11, 2006 to Mullani and U.S. Pat. No. 7,167,244 issued on Jan. 23, 2007 to Mullani, the substance of each of which is wholly incorporated herein by reference. The previously identified references disclose the combined use of white LEDs, UV/blue LEDs (405 nm), green/yellow LEDs (565 nm) and orange/red (630 nm). Alternatively, the U.S. Pat. Nos. 7,027,153 and 7,167,244 references suggest the use of LEDs with 480 nm, 580 nm and 660 nm wavelengths. In addition, a dermoscopy device identified as Dermlite® II Multispectral dermoscopy device manufactured and marketed by 3Gen, Inc. of San Juan Capistrano, Calif. provides four sets of LED's comprising white, blue light (470 nm) for surface pigmentation, yellow light (580 nm) for superficial vascularity viewing, and red light (660 nm) for viewing of pigmentation and vascularity with the deeper-penetrating red light frequency.

Dermatoscopes using coloured LEDS to augment the viewing of pigmentation of human tissue including skin is shown and described in U.S. Pat. No. 9,458,990 issued Oct. 4, 2016 to Mullani the substance of which is wholly incorporated herein by reference. In addition, a dermoscopy device identified as Dermlite® DL4 dermoscopy device manufactured and marketed by 3Gen, Inc. of San Juan Capistrano, Calif. provides combinations of white LED lights and orange LED lights in both polarized and non-polarized combinations to provide enhanced viewing of skin pigmentation.

Furthermore, hand-held medical illuminators have been used to introduce light into human tissue for observing sub-dermal structures using side-transillumination techniques whereby the light source is caused to be in direct contact with the skin to transfer light directly into the skin. One such technique is known and taught in U.S. Pat. No. 5,146,923 issued on Sep. 15, 1992 to Dhawan, the substance of which is wholly incorporated herein by reference. A combination of surface illumination, epiluminescence and transillumination apparatus and method is demonstrated in the Nevoscope™ product sold manufactured by Translite LLC, of Sugar Land, Tex. Another known apparatus and method of viewing vein structures beneath the skin employs the use of transillumination as described in U.S. Pat. No. 7,874,698 issued on Jan. 25, 2011 to Mullani the substance of which is wholly incorporated herein by reference. U.S. Pat. No. 7,874,698 issued to Mullani describes the use of orange light between 580 and 620 nm for transillumination imaging of deeper blood vessels in skin tissue.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

BRIEF SUMMARY

The inventive subject matter described herein demonstrates a multipurpose illuminator used in medical examinations. The multipurpose illuminator device described herein employs a housing incorporating two magnification viewing lenses each having different powered magnification that allows medical practitioners to view patient tissue and structures using two different magnifications. A battery power source is also contained in the housing to provide power to an illumination source. An illumination source may include an array of LEDs to provide light for viewing the patient tissue and other matter. The illumination source and the lenses may be cross polarized relative to each other to provide enhanced viewing of the patient tissues and structures. A switch is provided to initiate the LED illumination source or to provide modes of operation that provide certain of the LEDs being illuminated.

The described device may be used for multiple purposes. For example, a general medical practitioner may use the lower power magnifier to view or identify lesions or other items of interest on a patient. If a lesion or item of interest warrants closer examination, the practitioner can use the higher power magnifier. The polarized and/or cross polarized light of the device aids in reducing surface reflection. As shown in known dermoscopy devices, polarized and/or cross polarized light has been shown useful in viewing of skin lesions, however the same may also be useful in viewing other tissue and parts of the body not normally associated with dermatology practice. For example, the polarized and/or cross polarized light may be used in viewing wet skin surface areas, such as the back of the throat or in the patient's mouth.

The illumination device described herein may employ a spacer that may be selectively detachable in viewing alignment with a higher magnification lens to assist in holding the device stationary for detailed viewing of the patient tissue and structures. A protective sheath may be selectively detachable with the housing of the device to provide protection of the lenses when not in use. The sheath additionally includes a pocket clip for securing or holding the device on the person of the medical practitioner by attaching to a pocket, or a belt, or other garment. In addition, the protective sheath may be attached to the handle of the housing. Also, a metal plate may be affixed or formed about the viewing lenses of the device to assist in providing a magnetic attraction to adaptors that may be employed with cameras or cameras of smart phones.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 1 is a top perspective view of the illumination device described herein employing a sheath and spacer;

FIG. 2 is top perspective view of the illumination device described herein showing the sheath and spacer in a detached configuration;

FIG. 10 is a cross sectional view of the illumination device described herein along a longitudinal axis 10-10 shown in FIG. 7;

FIG. 11 is left side cross sectional view of the illumination device described herein along a longitudinal axis;

FIG. 12 is a top perspective view of the illumination device described herein showing a complimentary sheath;

FIG. 13 is a top perspective view of the illumination device described herein showing the complimentary sheath attached;

FIG. 14 is a top perspective view of the illumination device described herein wherein a metal plate is adapted to be placed adjacent the viewing lenses;

FIG. 15 is a top perspective view of the illumination device of FIG. 14 showing the metal plate in an exploded configuration; and FIG. 16 is a bottom perspective view of the metal plate shown in FIGS. 14 and 15.

DETAILED DESCRIPTION

Figure 3:
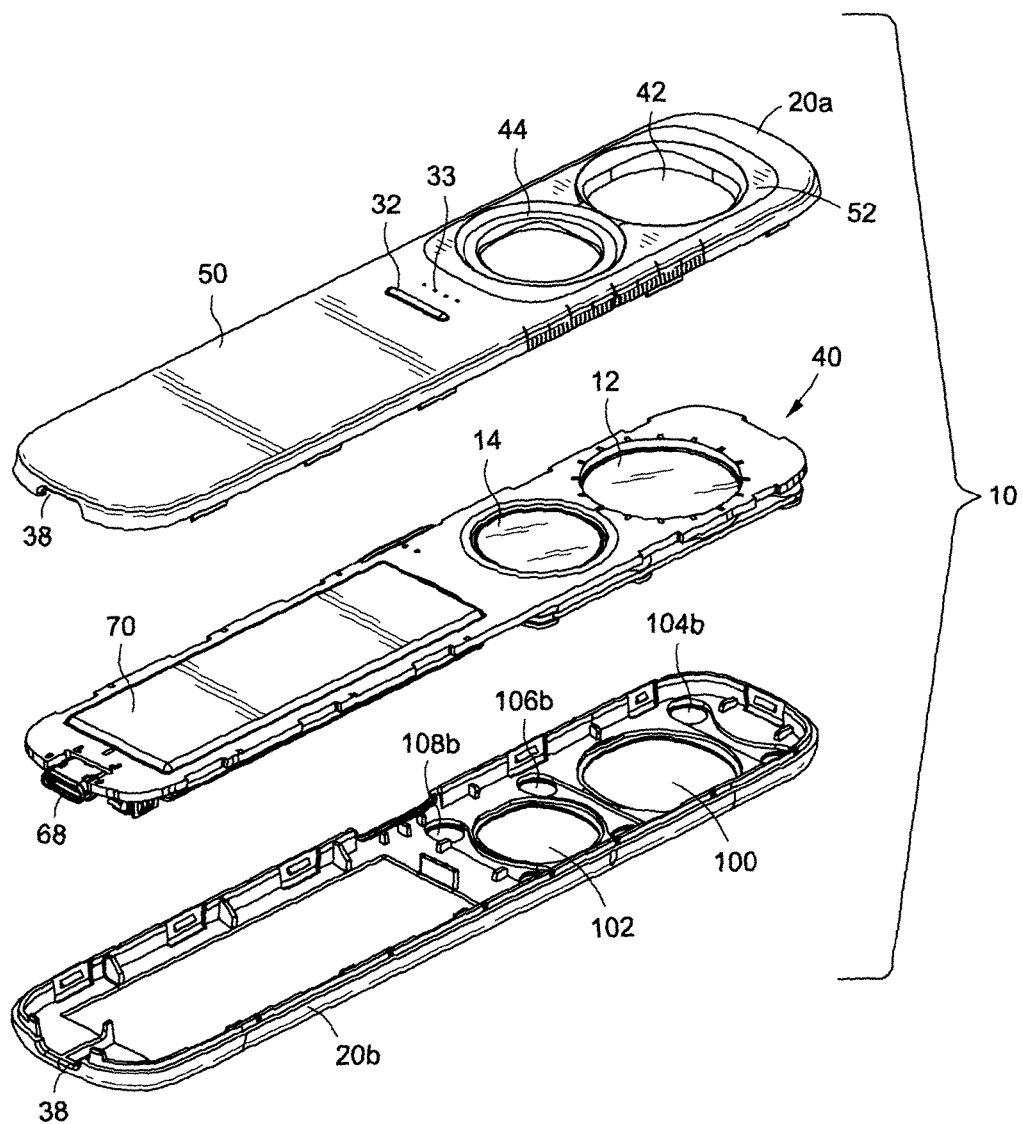
FIG. 3 is a top perspective exploded view of the components of the illumination device described herein.

The detailed description set forth below in connection with the appended drawings is intended as a description of certain embodiments of an illumination device and is not intended to represent the only forms that may be developed or utilized. The description sets forth the various structure and/or functions in connection with the illustrated embodiments, but it is to be understood, however, that the same or equivalent structure and/or functions may be accomplished by different embodiments that are also intended to be encompassed within the scope of the present disclosure. It is further understood that the use of relational terms such as first and second, and the like are used solely to distinguish one entity from another without necessarily requiring or implying any actual such relationship or order between such entities.

The background, summary and following description includes information that may be useful in understanding the present disclosure. It is not an admission that any of the information provided herein is prior art or relevant to the presently claimed inventive subject matter, or that any publication specifically or implicitly referenced is prior art.

Referring collectively to FIG. 1 and FIG. 2, there is shown the illumination device described herein. The illumination device 10 is a multipurpose medical examination tool that may allow medical practitioners to view patient tissue and structures using two different magnifications through two different powered lenses. The illumination device 10 includes two viewing lenses, namely, a first viewing lens 12 and a second viewing lens 14. The first viewing lens 12 provides magnification for use in medical examination. An eye 13 of the user views tissue and structures related to a patient undergoing medical examination through the viewing lens 12. It is contemplated that the viewing lens 12 may be useful in general practice medicine examinations. Polarized light and cross polarized viewing through lens 12 assists the examiner in viewing items of interest, since body tissue typically has translucent qualities, and polarized and cross-polarized light and magnification is known to be effective in medical examinations. The second viewing lens 14 also provides magnification at a higher magnification than the first viewing lens 12. An eye 15 of the user views tissue and structures related to a patient undergoing medical examination through viewing lens 14. Although FIG. 1 indicates operation of the device 10 through use of the naked eye of the user, it is contemplated herein that a camera or other optical device can also view tissue and matter through lenses 12 and 14. The first viewing lens 12 has a 1.43× magnification power and the second viewing lens 14 has a 6× magnification power. The disclosure contemplates that during medical examination, a medical practitioner may identify an area of interest using the viewing lens 12 and then switch to the higher magnification lens 14 for closer view. The polarized light and cross polarization assists viewing of tissue in both magnifications. The disclosure of the inventive subject matter herein contemplates that such magnification may vary for each of the viewing lenses 12 and 14. For instance, the first viewing lens 12 may be a large area exam lens with a lower magnification range between 1.2-3.0×, while the second viewing lens 14 may be a small area exam lens with a higher magnification range between 5.0-10.0×. The first viewing lens 12 may have a greater magnification than the second viewing lens 14. Also, one of the viewing lenses 12 or 14 may have no magnification.

In FIGS. 1 and 2, the illumination device 10 is shown interfacing with two accessory pieces, namely a spacer 16 and a protective sheath 18. The protective sheath 18 is also shown in FIGS. 11 and 12 interfacing with the device 10. The spacer 16 is adapted to interface the housing 20 to frictionally engage the housing 20 at housing recesses 22 (right side recess 22 shown in FIG. 2). A pair of complementary protrusions 24 (left side protrusion 24 shown in FIG. 2) are formed on an interior surface of the spacer 16 to frictionally engage recesses 22 of the housing 20 and snap fit on the housing 20. As such, the spacer 16 is selectively engageable with the housing 20 to be placed over the proximal side of the second viewing lens 14. Because of the high power of magnification of the viewing lens 14, the spacer 16 is useful in contacting the patient tissue 26 or the area to be viewed to keep the housing 20 and the viewing lens 14 steady to allow the user 15 to view the area of interest in detail. In this regard, the spacer 16 aids in holding the viewing lens 14 in a stationary position relative to the patient, which may be important with high magnification viewing or imaging because of the short focal distance. In the described device 10, an opening 17 in the spacer 16 may provide a direct viewing corridor for viewing tissue 26 or other items. In other embodiments of the described device, the opening 17 may include a glass faceplate for further stabilization and/or for conducing oil emersion viewing of tissue.

Referring collectively to FIGS. 1, 2, 12 and 13, a protective sheath 18 is shown interfacing with the device 10, namely the housing 20 of the device 10. As shown in FIG. 13, the protective sheath 18 is shown engaging and frictionally fitting over the housing 20 so as to cover and protect the operational components of the device 10, such as the viewing lenses 12 and 14 and the illumination array, namely the LEDs. In the attached configuration shown in FIG. 13, the sensitive viewing components such as lenses and LEDs are protected from incidental damage and from deleterious effects of other external items such as dust. The sheath 18 includes a complementary shape to the housing 20 and opening 28, formed in the sheath 18, and is adapted to receive the housing 20. A pair of recesses 30 (only one shown in FIG. 12) are adapted to engage a pair of housing protrusions (only the top protrusion 32 shown in FIG. 12). The two recesses 30 formed on the interior of the sheath 18, just inside the opening 28 frictionally engage a pair of housing protrusions 32 (one on each side of the housing 20) to enable the sheath 18 to cover the lenses 12, 14 and LEDs as demonstrated in FIG. 13. Likewise, the sheath 18 can be engaged to the reverse side of the housing 20 as shown in FIGS. 1 and 2. In FIG. 2, the sheath 18 is shown in exploded view and in FIG. 1, in an attached configuration to housing 20. The end of sheath 18, opposite of the opening 28 includes a connector opening 36. The connector opening 36 has a wider complementary opening to a charging port opening 38 on the housing 20, so that when the sheath 18 is engaged with the port opening 38 end of the housing 20, the sheath connector opening 36 is in corresponding alignment with the port opening 38 of the housing 20 to provide an unobstructed opening of the port opening 38 so that the device 10 can interface a male charging connector while the sheath 18 is attached to the housing 20. A clip 34 is formed on the sheath 18 to allow a user to fasten the sheath 18 when it is engaged to device 10 to a garment, belt, pocket or other similar structure to aid in preventing the device 10 from falling from the medical practitioner's pocket and becoming damaged. It is contemplated that the clip 34 could have a magnetized surface or embedded magnet to allow a user to magnetically secure the device 10 to a metal surface. Referring collectively to FIGS. 1 and 2, the illumination device 10 of the present disclosure is shown with a housing 20 that is adapted to be hand-held and to encase, among other things, a battery (not shown), lighting sources (not shown), and magnification lenses 12 and 14. The elongate housing 20 has a first handle end 21 and a second lens end 23. In operation, the medical practitioner holds the first handle end 21, viewing the tissue through the second lens end 23. Four LED indicators 33 display battery status, and battery charging status.

Figure 4:
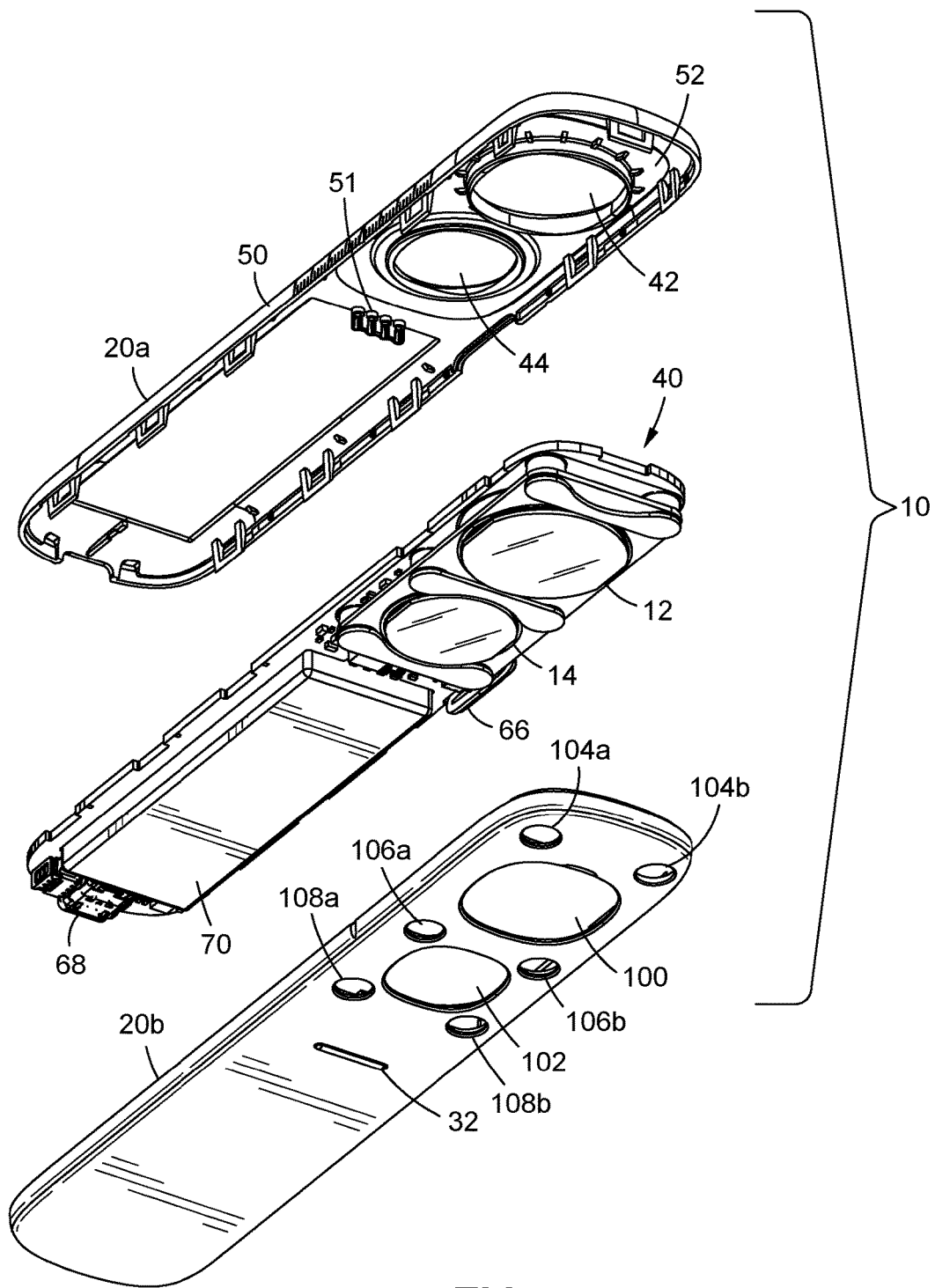
FIG. 4 a bottom perspective exploded view of the components of the illumination device described herein.

Referring to FIG. 3 and FIG. 4, exploded views of the device 10 are shown, with the housing 20 in separate pieces and including the internal components of the device 10. The housing 20, and other internal sub-assembly pieces of the structure of the device 10, are formed of assembled pieces of injection molded polycarbonate and polyurethane. It will be recognized by one skilled in the art that the housing 20 can be formed form other suitable rigid lightweight material, including, but not limited to plastic, composite materials, fiberglass, aluminum, PVC, acetate and or lexan. The housing 20 is formed of an upper body 20a and lower body 20b. The upper body 20a interfaces and connects to the lower body 20b to form the housing 20. The upper body 20a includes openings 42 and 44 to provide a visual opening to the incorporated lenses 12 and 14. Likewise, lower body 20b includes openings 100 and 102 corresponding to internal lenses 12 and 14. As such, a user may view patient tissue or matter by viewing through the openings 42 and 44, through internal lenses 12 and 14 and through lower body 20b openings 100 and 102, creating a line of sight in both viewing corridors. The upper body 20a may include a single, plastic component including an upper body frame 50 and an upper body eye port 52. The upper body eye port 52 may be overmolded in black plastic to reduce reflections. An internal components sub-assembly 40 nests between the upper body 20a and the lower body 20b. The internal components sub-assembly 40 is shown in exploded view with component parts in FIG. 5. Referring particularly to FIG. 4, the upper body 20a additionally includes light channel tubes 51 that transmit light from battery status and indicator LEDs (not shown) from the sub-assembly 40 to LED aperture indicators 33 (shown in FIG. 2) to allow a user to see battery status and charging status of battery 70. The sub-assembly 40 includes a USB type C connector 68 for mating with a male charger connector and providing power to the device and charging the battery. The LED indicators 33 which are for battery/charging status behave as follows: 4 indicator LEDs illuminate to show battery status during use wherein one illuminated LED indicates 0-25% battery remaining, two illuminated LEDs indicates 26-50% battery remaining, three illuminated LEDs indicates 51-75% battery remaining, and four illuminated LEDs 76-100% battery remaining. During charging, the LEDs pulse at 0.5 Hz to indicate active charging, wherein one pulsing LED indicates 0-25% battery charge, two pulsing LEDs indicate 26-50% battery charge, three pulsing LEDs indicates 51-75% battery charge, and four pulsing LEDs indicates 76-100% battery remaining. When all four LEDs are solid during charging, this indicates that the battery is fully charged.

Figure 5:
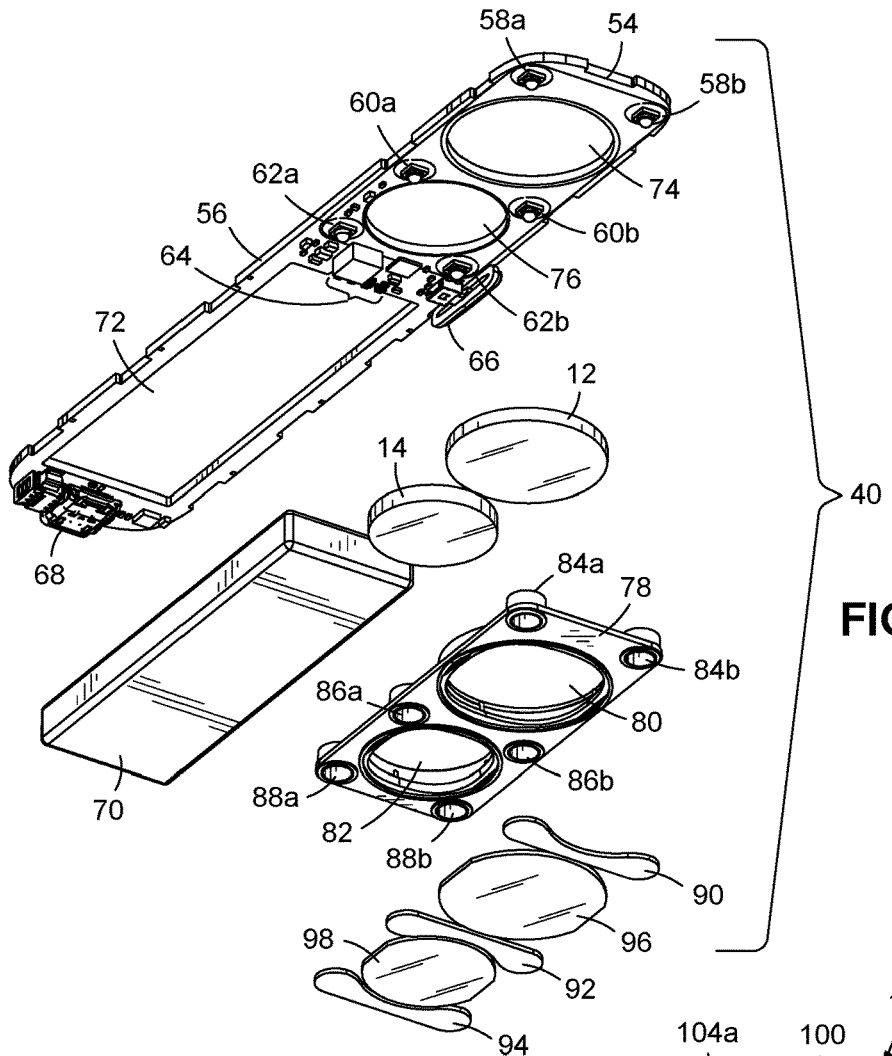
FIG. 5 is an exploded view of the internal assembly of the illumination device described herein.

Referring particularly to FIG. 5, there shown an exploded view of internal components sub-assembly 40. The internal components include printed circuit board ("PCB") assembly 54. The PCB assembly 54 includes a PCB 56 that include internal or surface electronic communication pathways or lead lines (not shown) that interconnect the various electronic components of the PCB assembly 54. A plurality of LEDs forming an LED array are affixed to and in electrical communication with the PCB 56. The LED array includes two upper LEDs 58a and 58b, two middle LEDs 60a and 60b, and two lower LEDs 62a and 62b. LEDs of the LED array may include high output solid state LEDs. The LEDs of the disclosure, 58a, 58b, 60a, 60b, 62a and 62b are high power surface mount white light LEDs. While the disclosed device contemplates use of white light for all six LEDs, it also contemplated that LEDs of differing colors may be used, with each LED being of a uniform color or the LED may include a mixture of different colored LEDs. In addition, while the disclosed device indicates use of four LEDs for each lens (totaling six LEDs) any suitable number of LEDs may be used for each set of LEDs for lenses 12 and 14 and positioned in the housing to provide an effective lighting for the device. Switching circuitry components 64 are also included on the PCB 56. Switching circuitry components 64 may include an LED driver, four surface mount LEDs for providing battery indication status to indicators 33 (FIG. 2) through light channels 51 (FIG. 4), battery controller chip, microprocessor and/or embedded software, interconnected with a physical button 66 interfaced with a switch (not shown). Switching circuitry components 64 permit the user to selectively activate various combinations of LEDs in the LED array. External button 66, provides a physical contact with an electrical switch (not shown) as part of the switching circuitry components 64 and such switch provides the mechanism for activating and deactivating all or sets of LEDs. In one embodiment, a press of the button 66 interfacing with the switch causes the upper LEDs 58a, 58b and middle LEDs 60a and 60b to activate and illuminate. This mode allows four LEDs surrounding the lens 12 to be activated and provide illumination for the lens 12. A second push of the button 66 causes the switch to deactivate upper LEDs 58a and 58b, while activating lower LEDs 62a and 62b, with middle LEDs 60a and 60b remaining activated. This mode allows the four LEDs surrounding the lens 14 to be activated and provide illumination to lens 14. Repeated pushing of the button 66 to cause the switch to toggle the illuminated LEDs to switch between the array of the low power lens 12 (58a, 58b, 60a, 60b) to higher power lens 14 (60a, 60b, 62a, 62b). Holding button 66 down and hence the switch for more than one second deactivates all LEDs. In a further embodiment, in addition to the two modes discussed above, another mode may turn all lights simultaneously upon a further push of the button 66 interfaced with the switch. In another embodiment, the button 66 interfaced with the switch may turn all of the LEDs on or off together. The PCB 56 also interconnects a power port 68, which is a USB type C port, to a battery 70 for charging the device 10 or for otherwise providing power to the device 10 through a USB charging chord or AC adapter, through a male connector (not shown) that interconnects to the power port 68. The battery 70 may interconnect to the power port 68 directly or through connections of the PCB 56, through known means to those skilled in the art. The battery 70 nests in PCB 56 opening 72. The battery 70 can be any rechargeable battery such as a lithium ion battery. The battery 70 is recharged through the power port 68, however, it is contemplated that the battery 70 could be charged using an inductive charging coil disposed within the housing 20 to enable charging of the portable power supply wirelessly.

The PCB 56 also includes openings 74 and 76 to provide a viewing corridor for lenses 12 and 14, respectively, and to be in cooperative alignment with openings 42 and 44 of upper body 20a (FIGS. 3 and 4) and openings 100 and 102 of the lower body 20b (FIGS. 3 and 4). Further, an optical assembly 78 is provided, having openings 80 and 82 to align with openings 74 and 76 of the PCB 56, respectively, and to interconnect with PCB 56. Lenses 12 and 14 nest within the openings 80 and 82 respectively. Lens 12 is a first power of 1.43× magnitude while lens 14 has a second power of 6× magnitude. Openings 84a and 84b are formed in the optical assembly 78 to provide a lighting corridor for LEDs 58a and 58b respectively to allow light from such LEDs to pass through from the PCB 56 through the optical assembly 78. Likewise, openings 86a and 86b are formed in the optical assembly 78 to provide a lighting corridor for LEDs 60a and 60b respectively to allow light from such LEDs to pass through from the PCB 56 through the optical assembly 78. Openings 88a and 88b are formed in the optical assembly 78 to provide a lighting corridor for LEDs 62a and 62b respectively to allow light from such LEDs to pass through from the PCB 56 through the optical assembly 78.

The assembly 40 additionally includes polarizers for the optical components. More particularly, a polarizer 90 provides a unitary structure that provides polarization to LEDs 58a and 58b, by covering the openings 84a and 84b. The result is polarized light emitted from LEDs 58a and 58b. Also, a polarizer 92 provides a unitary structure that provides polarization to LEDs 60a and 60b, by covering the openings 86a and 86b. The result is polarized light emitted from LEDs 60a and 60b. Also, a polarizer 94 provides a unitary structure that provides polarization to LEDs 62a and 62b, by covering the openings 88a and 88b. The result is polarized light emitted from LEDs 62a and 62b. Also, polarizer 96 is provided to cover opening 80 and thereby polarize any light transmitted through lens 12. Likewise, polarizer 98 is provided to cover opening 82 and thereby polarize any light transmitted through lens 14. Polarizers 96 and 98 are laminated with an acrylic bottom to aid in protecting the lenses. LED polarizers 90, 92 and 94 are cross-polarized relative to lens polarizers 96 and 98. It is contemplated in other embodiments of the device described herein where LED polarizers 90, 92 and 94 may be parallel polarized relative to lens polarizers 96 and 98. Also, other embodiment contemplate where the only LED polarizers 90, 92, 94 have only polarized light emitted, but without having the lenses polarized. Likewise, the disclosure contemplates that only lens polarizers 96 and 98 may be used without polarizing light from the LEDs. Finally, the disclosure contemplates that none of the optical components of the assembly 54 will use polarizers, and as such, the device 10 will be free of polarizing filters. In the described device, the polarizers are linear polarizers. In other embodiments, the lens polarizers and/or LED polarizers may be radially polarized.

Figure 6:
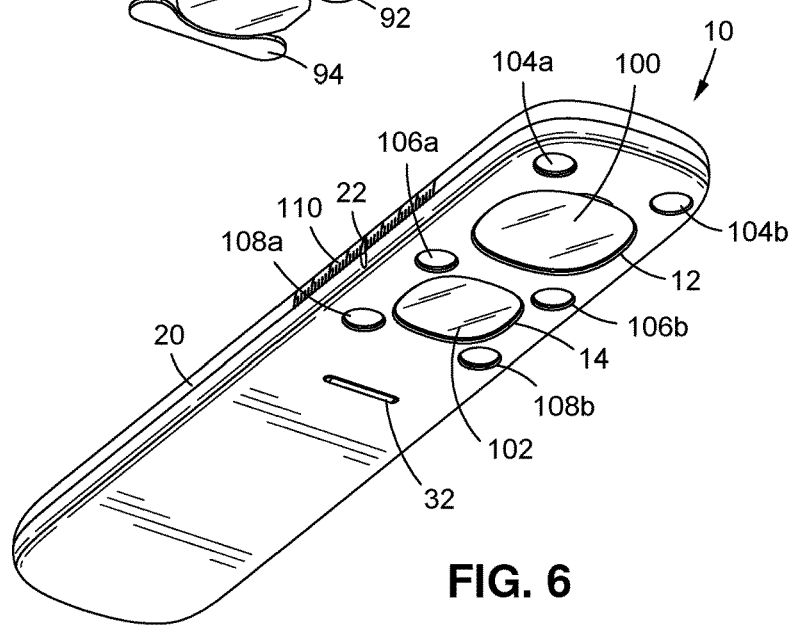
FIG. 6 is a bottom perspective view of the illumination device described herein.

Referring particularly to FIG. 6, there is shown a perspective lower view of the device 10 in the assembled configuration. FIG. 6 demonstrates the openings of the lower body 20b of the housing 20. The lower body 20b includes openings 100 and 102 to allow viewing through lenses 12 and 14 respectively. Openings 104a and 104b provide for the passage of light emanating from LEDs 58a and 58b, respectively. Openings 106a and 106b provide for the passage of light emanating from LEDs 60a and 60b, respectively. Openings 108a and 108b provide for the passage of light emanating from LEDs 62a and 62b, respectively. The surface of the housing 20 may also incorporate indicia of a scale 110 (shown in FIG. 2) to provide the user with information or measuring mechanism to understand or record measurements during the examination of a patient.

Figure 7:
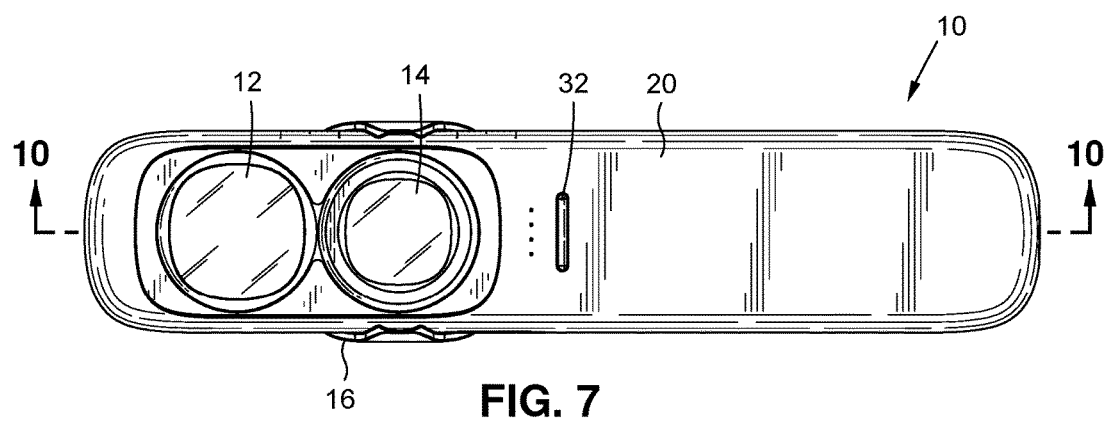
FIG. 7 is a top plan view of the illumination device described herein.
Figure 8:
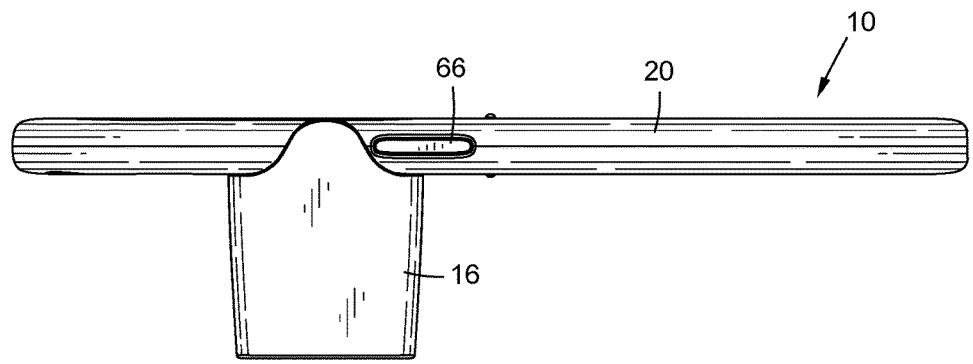
FIG. 8 is a left side view of the illumination device described herein.
Figure 9:
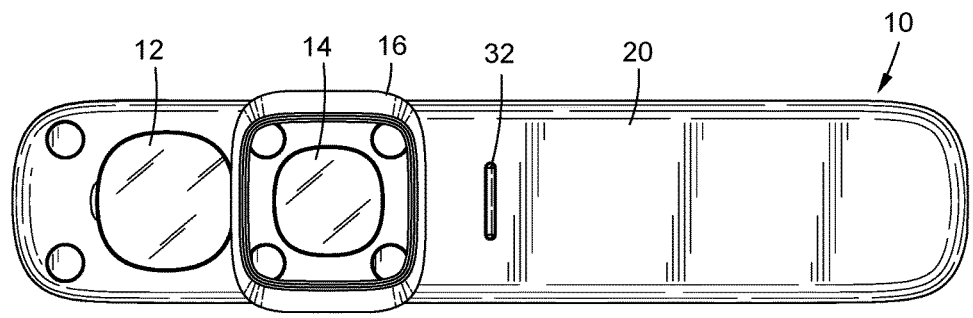
FIG. 9 is bottom plan view of the illumination device described herein with a spacer attached.

Referring particularly to FIGS. 7, 8, 9 and 10 there is shown the device 10 with spacer 16 attached, with FIG. 7 showing a top plan view, FIG. 8 showing a left side view, FIG. 9 showing a bottom plan view, and FIG. 10 showing a cross section of FIG. 7 along the axis 10-10. FIG. 10 is illustrative to disclose use of the device 10 in operation for high magnification viewing. The spacer 16 is deployed in FIG. 10, which most likely would be used by a user in highly magnified viewing through lens 14 that has a 6× magnification power. The spacer 16 stabilizes the device 10 against the subject matter 26 to be viewed through spacer opening 17. Viewer 15 views through opening 44 in the upper body housing 20a, through lens 14, and polarizer 98 to provide a polarized view through the lens 14. In the configuration where LEDs 62a/62b and 60a/60b are illuminated, the light passing through is filtered by LED filters 94 and 92 respectively, so that the light reaching the surface 26 is polarized. The polarized light is reflected back through filter 98 to the eye of user 15, and is cross polarized through filter 98. As is known in the art, cross polarized light from tissue surface enables the user to see deeper into the structures of skin or other tissue having translucent qualities.

With regard to FIG. 11, the spacer 16 is not deployed. As such, use of the device 10 without the spacer 16 more likely use the opening of the device 10 that uses the 1.43× lens 12. Viewer 13 views through opening 42 in the upper body housing 20a, through lens 12, and polarizer 96 to provide a polarized view through the lens 12. In the configuration where LEDs 58a/58b and 60a/60b are illuminated, the light passing through is filtered by LED filters 90 and 92 respectively, so that the light reaching the surface 26 is polarized. The polarized light is reflected back through filter 96 to the eye of user 13, and is cross polarized through filter 96. As is known in the art, cross polarized light from tissue surface enables the user to see deeper into the structures of skin or other tissue having translucent qualities, or otherwise may provide a better quality view than magnification without polarization.

Referring to FIGS. 14, 15 and 16 there is shown a further embodiment of the device 10 described herein including a metal faceplate 112. The faceplate 112 is applied to the surface of the housing 20 around the viewing lenses 12 and 14 of the device 10. The metal faceplate 112 can magnetically engage camera or smartphone adaptors that allow the camera lens to be used in the place of a human eye to record images that are viewed through the lenses 12 and 14. The faceplate 112 can be formed of 22-gauge steel sheet (0.75 mm) cold rolled 4130. The faceplate 112 can be metal stamped or formed from a CO2 or fiber laser cut, or from a CNC machine. The finish can be black oxide or bead blasted. An adhesive 114 can be applied to the back of the faceplate 112, wherein the adhesive is pressure sensitive adhesive such as 3M® 468MP pressure sensitive adhesive, applied up to 0.15 mm in thickness. In addition to the applying the metal plate 112 through an adhesive, is also contemplated that the plate 112 could be co-molded to the housing 20 around the lenses 12, 14.

In some embodiments, the numbers expressing dimensions, quantities, quantiles of ingredients, properties of materials, and so forth, used to describe and claim certain embodiments of the disclosure are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the disclosure are approximations, the numerical values set forth in the specific examples are reported as precisely as practicable. The numerical values presented in some embodiments of the disclose may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the disclosure and does not pose a limitation on the scope of the claimed inventive subject matter. No language in the specification should be construed as indicating any non-claimed element essential to the practice of the inventive subject matter.

Groupings of alternative elements or embodiments of the inventive subject matter disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed. Various objects, features, aspects and advantages of the inventive subject matter will become more apparent from the following detailed description of preferred embodiments, along with the accompanying drawing figures in which like numerals represent like components.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

The above description is given by way of example, and not limitation. Given the above disclosure, one skilled in the art could devise variations that are within the scope and spirit of the disclosure herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. An illumination device for non-contact illumination of organic tissue comprising:
    a housing;
    a first polarized lens assembly positioned in the housing and having a first lens and a first polarizer, the first lens being disposed about a first viewing axis and being of a first magnification power;
    a second polarized lens assembly positioned in the housing and having a second lens and a second polarizer, the second lens being disposed about a second viewing axis and being of a second magnification power, the first and second lenses being separate from each other and the first and second viewing axes being spaced apart from each other;
    at least one polarized light source positioned in the housing and including a light element and a light polarizer; and
    wherein either one or both of the first and second polarizers are cross-polarized relative to the at least one polarized light source.

2. The illumination device of claim 1, wherein the at least one polarized light source comprises:
    a first light source positioned in the housing to provide light for the first lens; and
    a second light source positioned in the housing to provide light for the second lens.

3. The illumination device of claim 2 wherein said first light source is an array of LEDs, and said second light source is an array of LEDs.

4. The illumination device of claim 3 wherein said array of LEDs of said first light source and the array of LEDs of the second light source share at least one LED.

5. The illumination device of claim 2 further comprising a switch in electrical communication with said light sources, said switch adapted to toggle each of the light sources off and on.

6. The illumination device of claim 2 wherein said first and second light sources each include at least one LED.

7. The illumination device of claim 6 wherein said LEDs are white light LEDs.

8. The illumination device of claim 2 wherein said first and second light sources each include at least one surface mount high power LED.

9. The illumination device of claim 1 further comprising a battery power source incorporated into said housing.

10. The illumination device of claim 1 wherein the first lens magnification is in the range of 1.2× to 3.0×.

11. The illumination device of claim 1 wherein the first lens magnification is 1.43×.

12. The illumination device of claim 1 wherein the second lens magnification is in the range of 5× to 10×.

13. The illumination device of claim 1 wherein the second lens magnification is 6×.

14. The illumination device of claim 1, wherein the housing includes a first opening, the first lens being optically aligned with the first opening.

15. The illumination device of claim 14, wherein the housing includes a second opening, the second lens being optically aligned with the second opening.

16. An illumination device for illumination of organic tissue, the illumination device comprising:
    a housing having a first opening defining a first axis and a second opening defining a second axis, the first and second openings being separate from each other and the first and second axes being spaced apart from each other;
    a first lens having a first magnification power coupled to the housing and in optical alignment with the first opening;
    a second lens having a second magnification power coupled to the housing and in optical alignment with the second opening, the second lens being separated from the first lens;
    a first lens polarizer in optical alignment with the first lens;
    a second lens polarizer in optical alignment with the second lens and separated from the first lens polarizer;
    a plurality of light sources coupled to the housing; and
    at least one light source polarizer in alignment with at least one of the plurality of light sources for polarizing at least a portion of the light emitted from the at least one of the plurality of light sources.

17. The illumination device of claim 16, wherein the plurality of light sources includes a first pair of light sources arranged in diametrically opposed relation to the first lens.

18. The illumination device of claim 17, wherein the plurality of light sources includes a second pair of light sources arranged in diametrically opposed relation to the second lens.

19. The illumination device of claim 18, wherein the first pair of light sources and the second pair of light sources includes a common light source.

20. The illumination device of claim 16, wherein the housing includes a plurality of openings in optical alignment with respective ones of the plurality of light sources.

21. An illumination device for illumination of organic tissue, the illumination device comprising:
- a housing having first and second openings;
- a first lens having a first magnification power coupled to the housing and in optical alignment with the first opening;
- a second lens having a second magnification power coupled to the housing and in optical alignment with the second opening, the second lens being separated from the first lens;
- at least one lens polarizer in optical alignment with either one or both of the first lens and the second lens;
- a plurality of light sources coupled to the housing and including a first pair of light sources arranged in diametrically opposed relation to the first lens, a second pair of light sources arranged in diametrically opposed relation to the second lens, wherein the first pair of light sources and the second pair of light sources includes a common light source; and
- at least one light source polarizer in alignment with at least one of the plurality of light sources for polarizing at least a portion of the light emitted from the at least one of the plurality of light sources.

22. An illumination device for illumination of organic tissue, the illumination device comprising:
- a housing having first and second openings;
- a first lens having a first magnification power coupled to the housing and in optical alignment with the first opening;
- a second lens having a second magnification power coupled to the housing and in optical alignment with the second opening, the second lens being separated from the first lens;
- a first lens polarizer in optical alignment with the first lens;
- a second lens polarizer in optical alignment with the second lens and separated from the first lens polarizer;
- a plurality of light sources coupled to the housing, the plurality of light sources including a first pair of light sources arranged in diametrically opposed relation to the first lens and a second pair of light sources arranged in diametrically opposed relation to the second lens, the first pair of light sources and the second pair of light sources including a common light source; and
- at least one light source polarizer in alignment with at least one of the plurality of light sources for polarizing at least a portion of the light emitted from the at least one of the plurality of light sources.

* * * * *